United States Patent
Frings

(10) Patent No.: US 10,357,268 B2
(45) Date of Patent: Jul. 23, 2019

(54) ROTABLE AND PIVOTABLE MEDICAL INSTRUMENT

(71) Applicant: Karl Storz SE & Co. KG, Tuttlingen (DE)

(72) Inventor: Hermann-Josef Frings, Aachen (DE)

(73) Assignee: Karl Storz SE & Co. KG, Tuttlingen (DE)

(*) Notice: Subject to any disclaimer, the term of this patent is extended or adjusted under 35 U.S.C. 154(b) by 416 days.

(21) Appl. No.: 14/575,736

(22) Filed: Dec. 18, 2014

(65) Prior Publication Data

US 2015/0173786 A1   Jun. 25, 2015

(30) Foreign Application Priority Data

Dec. 19, 2013 (DE) .................. 10 2013 114 556

(51) Int. Cl.
  *A61B 17/29* (2006.01)
  *A61B 17/00* (2006.01)
  *A61B 17/28* (2006.01)

(52) U.S. Cl.
  CPC .......... *A61B 17/282* (2013.01); *A61B 17/29* (2013.01); *A61B 2017/00398* (2013.01);
  (Continued)

(58) Field of Classification Search
  CPC .............. A61B 17/068; A61B 17/0682; A61B 17/0684; A61B 17/0686; A61B 17/072;
  (Continued)

(56) References Cited

U.S. PATENT DOCUMENTS

| 1,754,806 A | * | 4/1930 | Stevenson | .......... A61B 17/1608 |
| | | | | 30/229 |
| 4,038,987 A | * | 8/1977 | Komiya | ............... A61B 17/122 |
| | | | | 606/142 |

(Continued)

FOREIGN PATENT DOCUMENTS

| CN | 103908320 A | 7/2014 |
| DE | 9302650 U1 | 4/1993 |
| WO | 2010112608 A1 | 10/2010 |

OTHER PUBLICATIONS

Great Britain Search Report Application No. GB1421584.2 Completed: May 18, 2015; dated May 19, 2015; 3 pages.

(Continued)

*Primary Examiner* — Dianne Dornbusch
(74) *Attorney, Agent, or Firm* — Whitmyer IP Group LLC

(57) ABSTRACT

A medical instrument has a shaft, which has a distal end and a proximal end, with a jaw head which is arranged at the distal end and is pivotable out from the longitudinal axis of the shaft, wherein the jaw head has two jaw parts, of which at least one is pivotable, furthermore, with a first actuation element for pivoting the jaw head, and with a second actuation element for pivoting the pivotable jaw part, wherein the actuation elements are received in the shaft, and with control elements which are arranged at the proximal end of the shaft and are used for controlling the movement of the actuation elements. The actuation elements are arranged extending coaxially with respect to each other, and that the actuation elements are received in the shaft so as to be rotatable jointly about the shaft axis and to be rotatable relative to the shaft.

18 Claims, 4 Drawing Sheets

(52) U.S. Cl.
CPC . *A61B 2017/294* (2013.01); *A61B 2017/2927* (2013.01); *A61B 2017/2929* (2013.01)

(58) Field of Classification Search
CPC . A61B 17/28; A61B 17/2804; A61B 17/2812; A61B 17/2816; A61B 17/29; A61B 2017/2927; A61B 2017/2929; A61B 2017/2932; A61B 2017/2938; A61B 2017/2939; A61B 2017/2947
See application file for complete search history.

(56) References Cited

U.S. PATENT DOCUMENTS

| | | | | |
|---|---|---|---|---|
| 4,672,964 A * | 6/1987 | Dee | A61B 17/3213 | 30/321 |
| 4,712,545 A * | 12/1987 | Honkanen | A61B 17/1608 | 600/564 |
| 4,785,825 A * | 11/1988 | Romaniuk | A61B 10/02 | 600/564 |
| 4,872,456 A * | 10/1989 | Hasson | A61B 17/2812 | 606/207 |
| 5,133,727 A * | 7/1992 | Bales | A61B 17/29 | 600/562 |
| 5,133,735 A * | 7/1992 | Slater | A61B 17/2909 | 600/564 |
| 5,176,702 A * | 1/1993 | Bales | A61B 17/29 | 600/564 |
| 5,215,101 A * | 6/1993 | Jacobs | A61B 10/06 | 600/562 |
| 5,234,453 A * | 8/1993 | Smith | A61B 10/06 | 606/170 |
| 5,241,968 A * | 9/1993 | Slater | A61B 10/06 | 600/564 |
| 5,254,130 A * | 10/1993 | Poncet | A61B 17/29 | 600/564 |
| 5,290,308 A * | 3/1994 | Knight | A61B 17/29 | 604/247 |
| 5,290,309 A * | 3/1994 | Kothe | A61B 17/2833 | 606/207 |
| 5,300,087 A * | 4/1994 | Knoepfler | A61B 17/29 | 604/33 |
| 5,350,391 A * | 9/1994 | Iacovelli | A61B 17/320016 | 606/167 |
| 5,374,277 A * | 12/1994 | Hassler | A61B 17/29 | 606/170 |
| 5,383,888 A * | 1/1995 | Zvenyatsky | A61B 17/0218 | 600/564 |
| 5,474,571 A * | 12/1995 | Lang | A61B 17/29 | 606/174 |
| 5,582,617 A * | 12/1996 | Klieman | A61B 17/29 | 606/170 |
| 5,752,973 A * | 5/1998 | Kieturakis | A61B 17/29 | 606/205 |
| 8,419,720 B1 * | 4/2013 | Dawoodjee | A61B 17/29 | 600/104 |
| 8,496,656 B2 * | 7/2013 | Shields | A61B 18/1445 | 606/51 |
| 8,568,443 B1 * | 10/2013 | Jackman | A61B 17/00 | 606/157 |
| 8,579,897 B2 * | 11/2013 | Vakharia | A61B 18/1445 | 606/207 |
| 8,641,713 B2 * | 2/2014 | Johnson | A61B 17/29 | 606/206 |
| 8,721,640 B2 * | 5/2014 | Taylor | A61B 18/1445 | 606/171 |
| 8,752,699 B2 * | 6/2014 | Morgan | A61B 90/92 | 206/339 |
| 8,771,260 B2 * | 7/2014 | Conlon | A61B 17/29 | 606/1 |
| 8,893,949 B2 * | 11/2014 | Shelton, IV | A61B 90/92 | 227/175.1 |
| 9,585,651 B2 * | 3/2017 | Lam | A61B 17/0401 | |
| 9,622,763 B2 * | 4/2017 | van den Dool | A61B 17/29 | |
| 2005/0049633 A1 * | 3/2005 | Watanabe | A61B 10/06 | 606/205 |
| 2007/0208375 A1 * | 9/2007 | Nishizawa | A61B 17/29 | 606/205 |
| 2007/0288044 A1 * | 12/2007 | Jinno | A61B 17/29 | 606/174 |
| 2008/0171908 A1 * | 7/2008 | Okada | A61B 10/04 | 600/114 |
| 2010/0179540 A1 * | 7/2010 | Marczyk | A61B 18/1445 | 606/41 |
| 2011/0106078 A1 * | 5/2011 | Mueller | A61B 17/29 | 606/52 |
| 2012/0022554 A1 * | 1/2012 | Paik | A61B 17/29 | 606/130 |
| 2012/0078292 A1 * | 3/2012 | Banju | A61B 17/1227 | 606/206 |
| 2012/0083770 A1 * | 4/2012 | Paik | A61B 17/29 | 606/1 |
| 2012/0234893 A1 * | 9/2012 | Schuckmann | A61B 17/07207 | 227/175.2 |
| 2012/0259331 A1 * | 10/2012 | Garrison | A61B 18/1445 | 606/51 |
| 2013/0304083 A1 * | 11/2013 | Kaercher | A61B 17/00 | 606/130 |

OTHER PUBLICATIONS

German Examination Report Application No. 102014117393.7 dated Jul. 22, 2016;Receipt Date: Jul. 27, 2016 7 pages.

* cited by examiner

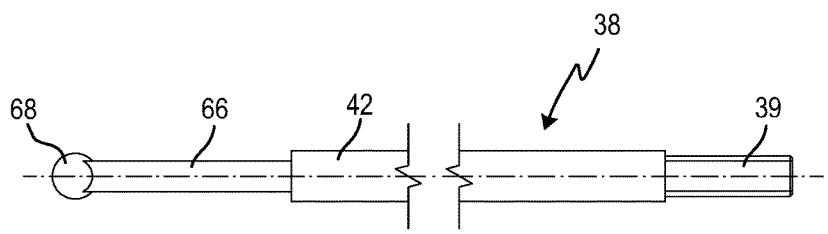
Fig. 6
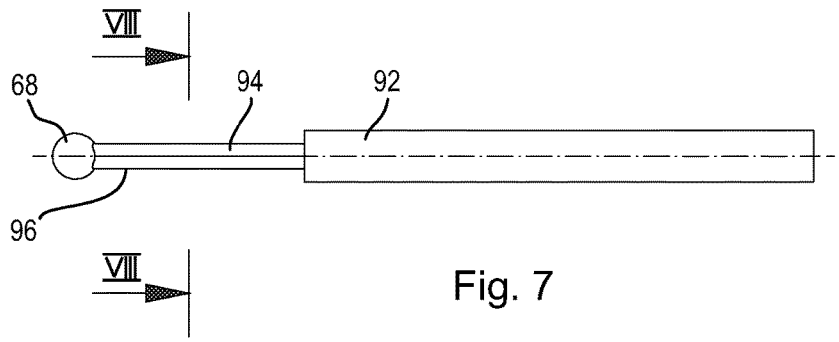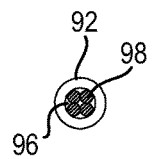
Fig. 7
Fig. 8
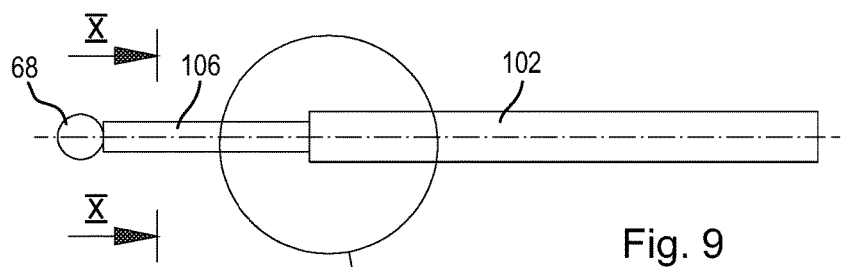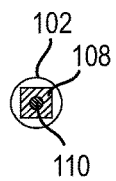
Fig. 9
Fig. 10
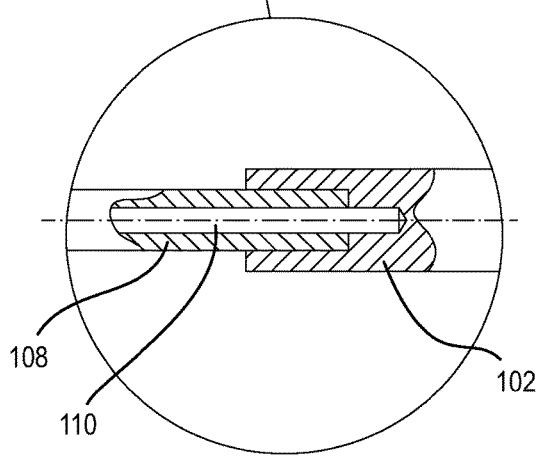

ROTABLE AND PIVOTABLE MEDICAL INSTRUMENT

FIELD OF THE INVENTION

The invention relates to a medical instrument with a shaft, which has a distal end and a proximal end, with a jaw head which is arranged at the distal end and is pivotable out from the longitudinal axis of the shaft.

BACKGROUND OF THE INVENTION

A medical instrument of this kind is known from DE 93 02 650 U1.

The known medical instrument is designed in the form of medical forceps. A jaw head is arranged at the distal end of an elongate rigid shaft and is pivotable out from the longitudinal axis of the shaft. The jaw head has a rigid jaw part and a pivotable jaw part.

To pivot the jaw head, the latter is connected to a first actuation element in the form of a wire, which is guided all the way through the shaft to the proximal end. There, the wire is connected to a movable grip part of a scissor-like handle. This movable grip part represents a control element by which this wire can be moved axially to and fro in the shaft in order to pivot the jaw head. The design is such that, in a first range of movement of the grip element, both jaw parts are pivoted together, i.e. the entire jaw head is pivoted. In a second range of movement following on from the first one, the movable jaw part can be moved relative to the stationary jaw part, i.e. can be opened and closed. For this purpose, a second actuation element in the form of a further wire is present, which is connected at the distal end to the pivotable jaw part and connected at the proximal end to the pivotable grip element. The two wires extend alongside each other in the shaft.

Instruments of this kind are used, for example, in procedures in the maxillary sinus, in order to remove a section of tissue, for example a cyst or cartilage. For insertion, the distal end can be pushed into the nasal opening and introduced into the maxillary sinus through an aperture, a so-called window, provided in the nasal wall. The pivotability of the jaw head means that the latter can initially be oriented in a relatively rectilinear manner with respect to the shaft during insertion into the nasal cavity, and can be pivoted, with the jaw parts still closed, only upon insertion into the maxillary sinus. In this way, the jaw head can be brought to places lying to one side in relation to the direction of insertion through the nasal opening. The jaw parts are then opened and placed on the tissue to be separated, and a piece of tissue is separated by closure of the jaw parts.

If the tissue is cartilage, considerable forces have to be applied in order to separate a section of cartilage.

These are relatively slender medical instruments which, on the one hand, are intended to permit the greatest possible number of degrees of freedom of orientation of the jaw head and of the jaw parts with respect to the orientation of the shaft. On the other hand, the aim is to allow considerable forces to be transmitted despite the slender design.

In the medical forceps mentioned at the outset, the two wires of the actuation elements are arranged alongside each other in the shaft and lie spaced apart from each other and so take up quite a lot of space. A further disadvantage is that, in a first range of movement of a control element, the jaw head can only be pivoted, and it is only possible for the jaw parts to be opened and closed after this pivoting movement has been performed.

From U.S. Pat. No. 8,419,720 B1 a medical instrument is known whose outer rod has an articulated section at its distal end. For controlling the articulation a hollow actuation rod is disposed within the outer rod. The actuation rod is connected to a tension element within the articulation section of the outer rod. The actuation rod causes the articulated section to bend when tension is applied.

An attachment rod is inserted into the actuation rod. The attachment rod supports a jaw head at its distal end and has movable jaw parts. The jaw head has an outer thread configured to couple with an inner thread of the outer rod at its distal end. That connection provides a specific fixed rotational orientation of the jaw head relative to the outer rod. An axial movement of the attachment rod causes a closing and opening of the jaw parts.

The object of the present invention is therefore to further develop a medical instrument of the type mentioned at the outset in such a way that, while having a slender design, it is able to exert considerable forces, particularly during closure of the jaw parts, and additionally provides a high degree of freedom of the possible movements of jaw head and jaw parts relative to the shaft.

SUMMARY OF THE INVENTION

The object is achieved by a medical instrument, comprising a hollow shaft having a distal end and a proximal end, a jaw head arranged at said distal end of said shaft, said jaw head having two jaw parts, at least one of said two jaw parts is pivotable, said jaw head together with said two jaw parts being pivotable out from a longitudinal axis of said shaft, a first actuation element for pivoting said jaw head out from that longitudinal axis, at least one second actuation element for pivoting said at least one pivotable jaw part, said actuation elements are housed in said hollow shaft, control elements arranged at said proximal end of said shaft, said control elements are for controlling a movement of said actuation elements housed in said shaft, wherein said actuation elements being arranged coaxially with respect to each other within said shaft, and wherein said actuation elements are jointly rotatable about said shaft axis, and wherein said jointly rotatable actuation elements are rotatably relative to said shaft.

The coaxial design allows the two actuation elements to be arranged within a very narrow space in the shaft, such that extremely slender shafts are possible. The coaxial design opens up the possibility of providing an inner central actuation element which consists of a compact rod-shaped body with tensile and compressive strength, for example in the form of a wire or a rod. Through this compact body it is possible to transmit relatively high compressive and tensile forces, which are needed to close the movable jaw part with the necessary force such that the tissue held in between, for example cartilage, can be severed. The further actuation element, which coaxially surrounds the central actuation element, can be designed for example as a tubular body which, by virtue of its geometry, can exert relatively high tensile and compressive forces. This outer actuation element can be used to pivot the jaw head. The forces needed for this are substantially less than the forces for closing a jaw part. However, the pivotable jaw part can be opposed by the corresponding abutment against which the closing movable jaw part strikes. The outer element can, however, be made with a relatively thin wall. This results overall in an extremely slender design of the shaft. In addition, it is possible for the jaw head area to be made relatively short.

Providing the possibility of designing these two actuation elements in the shaft to be rotatable jointly about the shaft axis has the advantage of affording a further degree of freedom of the orientation of the jaw head relative to the shaft, namely by rotation of the actuation elements.

This results in the advantage to rotate the two actuation elements without rotating the shaft. If the shaft is pushed into a maxillary sinus, for example, and if the jaw head has already been brought to a defined pivoted or angled position relative to the shaft, this already angled or still rectilinearly oriented jaw head can be pivoted about the shaft axis, so as to be brought to an optimal position for separating the tissue. This can be done in a way that is particularly atraumatic for the patient, since the shaft, already placed in the narrow space in the nose for example, does not have to be rotated in this movement; instead, it is the actuation elements received therein, and used for moving the jaw head and the jaw parts, that have to be rotated.

The feature whereby these two actuation elements are received so as to be jointly rotatable in the shaft axis has the considerable advantage that the rotation of one actuation element automatically also effects the co-rotation of the other actuation element. The control elements for actuating the actuation elements can have various configurations. Thus, they can be mechanical control elements such as grip parts. They can also be motor-driven control elements or parts of movement robots.

Returning to the aforementioned configuration in which a relatively compact, central rod-shaped first actuation element is present, the control element providing for the rotation can be mounted thereon. It is thus ensured that this rotation movement is transmitted directly, without the danger of even a relatively thin actuation element twisting. By virtue of the fact that the other actuation element is also co-rotated at the same time in this rotation movement, a corresponding control element does not have to be mounted on this second actuation element again. In addition, this has the advantage that the two actuation elements are always arranged in an unchanged position of rotation relative to each other, the result of which is that the pivoting of the jaw part relative to the jaw head always takes place in the same plane in any desired position of rotation of the jaw head.

The two actuation elements are of course axially movable relative to each other. Not only is this easily possible in a coaxial arrangement, this coaxial arrangement, seen along the length of the shaft, also at the same time opens up the possibility of guiding these axial movements well. This can be achieved, for example, by the centrally located actuation element being designed as a rod-shaped body, onto the outside of which a corresponding sleeve or tubular body is pushed with a matching fit.

The joint rotatability can be obtained without great outlay, by form-fit engagement means being provided between the two actuation elements, which means permit an axial movement but block a rotation of the two actuation elements relative to each other.

Overall, by relatively simple design measures, it is possible to obtain relatively slender shafts via which high forces can be applied to the jaw parts, while numerous degrees of freedom are at the same time made available to the operator for orienting the jaw head relative to the shaft and for moving the jaw parts in each of these possible orientations, i.e. independently thereof. The area of use of such instruments is in particular in minimally invasive surgery, such as laparoscopy, arthroscopy, etc. Most of the spaces in the interior of living bodies are very restricted, such that instruments with so many degrees of freedom can also be applied in places that are difficult to access.

To achieve this with the simplest possible design, a further embodiment of the invention proposes that the actuation elements are movable relative to each other, and independently of each other, along the shaft axis, but are connected to each other in a rotationally conjoint manner about the shaft axis.

In another particularly advantageous embodiment, the rotationally conjoint connection is such that a rotation of one of the actuation elements about the shaft axis causes a rotation of the other actuation element.

This measure has the advantage that both actuation elements can be rotated together about the longitudinal axis by a single control element. In principle, the control element can also be designed such that it is connected to both actuation elements, thereby effecting the joint pivoting. Since, as has already been mentioned, the coaxial arrangement makes it possible to provide a torsionally resistant, central rod-shaped actuation element, it is structurally simpler to connect the control element to this actuation element and to provide measures to ensure that, when this element is rotated, the other one is automatically co-rotated. Since no great forces have to be applied here, this can also be achieved if the outer, second actuation element arranged coaxially around the central element has a relatively thin wall.

In another embodiment of the invention, the first actuation element is connected to a first control element, by which the axial movement of the first actuation element can be effected, and the at least one second actuation element is connected to a second control element, by which the axial movement of this actuation element can be effected independently of the first actuation element.

This increases the manoeuvrability, particularly in relation to the aforementioned prior art, since the jaw head can be pivoted with respect to the shaft axis irrespective of the position in which the jaw part is located. At the same time, the at least one movable jaw part can be opened and closed irrespective of the pivoting position in which the jaw head is located relative to the shaft.

If both jaw parts are movable, then two second actuation elements are correspondingly present. An intermediate joint can also be provided, for example a toggle joint, so that both jaw parts can be moved in synchrony by one actuation element. However, the basic principle remains the same, i.e. the movement of the jaw head is independent of the movement of the one or two movable jaw parts.

In another embodiment of the invention, a further control element is present, by which a rotation of the actuation elements in the shaft about the longitudinal axis can be effected independently of the control elements for the axial movement.

This measure has the advantage that the degrees of freedom for manoeuvring are increased, such that this further control element affords the operator the possibility of additionally rotating the two actuation elements, and therefore the jaw head and the jaw parts, and of doing so irrespective of the relative axial position of movement in which the actuation elements are located in relation to each other.

This also has the advantage of helping orientate the operator such that, when he wants to be occupied only with the axial movement of the actuation elements, he concentrates on those control elements via which the pivoting of the jaw head and the relative pivoting of at least one jaw part can be effected. In most cases, he will of course carry out these manoeuvres when he has already oriented the jaw head in a favourable position for the separation process. For the rotation movement, it is ergonomic to provide a further control element which serves exclusively to rotate the actuation elements, and therefore the jaw head, relative to the shaft.

In another embodiment, the possibility already mentioned above is achieved, namely that the first actuation element for pivoting the jaw head is arranged coaxially around the one or more actuation elements for pivoting the two jaw parts. As has already been mentioned, this makes it possible, even when the shaft is of an extremely slender design, to provide relatively stable second actuation elements for opening and closing the jaw parts, these second actuation elements being closely surrounded coaxially by the first actuation element for pivoting the jaw head.

In another embodiment of the invention, the actuation elements are coaxially insertable one inside the other and, in one axial length portion, have a non-circular cross section, which effects the rotationally conjoint connection.

The insertion of the actuation elements one inside the other permits simple assembly and dismantling of these actuation elements. Moreover, this simplifies the introduction of the unit composed of the actuation elements in the shaft, specifically by means of this whole unit being pushed as a kind of work insert into the shaft. The rotationally conjoint connection is effected by the particular cross-sectional shape, for example as a polygon or as an oval, etc. This ensures that the rotation of one actuation element about the longitudinal axis of the shaft causes the rotation of the other one as well.

In another embodiment of the invention, the jaw head has a stationary jaw part and a pivotable jaw part, wherein the pivotable jaw part is connected to a flexible distal end portion of a pull/push rod arranged centrally in the shaft.

This measure has the advantage that the flexible distal end portion can be suitably curved in order to effect or to follow the pivoting movement of the pivotable jaw part. This design also helps ensure that the jaw head can be made relatively short.

In order to obtain a pivoting movement, it is of course customary to arrange the distal end of the actuation element at a slight distance from the pivot axis of the pivotable jaw part. This distance then acts like a lever, in order to transmit the corresponding torque. Since the pivotable jaw part is pivoted about a fixed pivot axis on the jaw head, and since the distal end of this actuation element is arranged at a distance therefrom, the latter has to follow a curved path during the pivoting. For example, should the opening angle between pivotable jaw part and stationary jaw part be more than 90°, this is a relatively long distance that the flexible distal end portion has to travel.

This opens up the possibility for the central pull/push rod, in so far as it is located in the shaft, to be designed as a rigid and stiff body and to be provided with a distal end area which, although also being able to transmit compressive and tensile forces, has a sufficient flexibility to follow the pivoting movements of the movable jaw part.

In another embodiment of the invention, the first actuation element is designed as a tubular body which surrounds the pull/push rod, wherein the tubular body has a flexible distal continuation, which is connected to the jaw head.

This measure has the advantage that the flexible continuation is able to follow the pivoting movements of the jaw head.

In principle, this pivoting movement takes place mechanically in the same way as the pivoting movement of the jaw part.

That is to say, the distal end of this first actuation element, i.e. the distal end of the distal continuation, is arranged at a slight distance from the pivot axis of the jaw head, in order to obtain the corresponding lever action. To ensure now that this distally outermost articulation point between the first actuation element and the pivotable jaw head is able to follow the pivoting movement, the axial continuation of the tubular body is made flexible. The tubular body does not have to be flexible in the area in which it is received in the shaft itself, since in this area it of course only performs the axial movements. This opens up the possibility of designing this tubular body as a relatively thin but generally stiff sleeve which is pushed with a close fit, but movably, onto the outside of the central actuation element. Since, as has already been mentioned a number of times, the forces for pivoting the jaw head are substantially less than the required closing forces of the jaw parts upon separation of tissue, both the tubular body and also in particular the flexible distal continuation can be made relatively thin. This also opens up the possibility of producing this first actuation element from a shaped body of pliable but still relatively stiff plastic, which can be produced as an entire component, for example designing it as an injection-moulded part, or of designing it first as a tubular body which is worked, by removal of material, such that a tongue-shaped flexible distal continuation protrudes therefrom. Metallic as well as plastic materials are suitable for this purpose.

In another embodiment of the invention, the control elements are arranged at the proximal end area of the shaft.

This measure has the advantage of making the handling of the medical instrument easier.

In another embodiment of the invention, a forceps-like handle with a stationary grip part and a movable grip part is arranged at the proximal end of the shaft, wherein the movable grip part is connected to the second actuation element for pivoting the pivotable jaw part and controls the movement thereof.

This measure has the advantage of providing the operator with a scissor-like handle, a construction which is very common in instrument design and with which operators are familiar. The movable grip part of course moves the actuation element that moves the pivotable jaw part. It is precisely with this jaw part of course that the considerable forces have to be exerted in order, for example, to separate a hard cartilage section. The operator can then take up the forceps-like handle in one hand in such a way that, for example, the thumb is placed in the movable grip part and this force is applied by the thumb.

In another embodiment of the invention, the second axially movable actuation element for pivoting the movable jaw part has a proximal end portion, on which the further control element is mounted, by which the second axially movable actuation element is rotatable about the shaft axis.

This measure has the considerable advantage that, by means of one control element, for example the above-described movable grip part, this second actuation element can be moved axially to and fro in order to separate a tissue part. The further control element, mounted on the same actuation element, namely on the distal end area thereof, allows the operator to rotate the two actuation elements.

He can either do this with the same hand holding the instrument or with his other hand.

This permits particularly precise and fine adjustment, for example by the jaw head being pivoted relative to the shaft axis with the first actuation element and, by manipulation with the further control element, also being rotated about the longitudinal axis of the shaft.

In another embodiment of the invention, a further movable grip part is mounted on the proximal end area of the shaft, which grip part is connected to the first actuation element and controls the movement thereof.

The first, stationary grip part of the handle is as it were the fixed reference point relative to which the second grip part can be moved. By providing a further movable grip part, it is now also possible to move this further movable grip part relative to the stationary grip part. Thus, the one movable grip part can be used to control the movement for example of the one or more second actuation elements for opening and closing the jaw parts, and the further movable grip part can be used to control the movement of the first actuation element, namely for pivoting the jaw head.

By a suitably ergonomic arrangement of the two movable grip parts on the handle, they can be moved by different fingers of the hand that is holding the instrument. For example, the middle finger of one hand can be placed in the stationary grip part, the thumb in the movable grip part that moves the second actuation element for pivoting the jaw part, and the ring finger or the little finger in the further movable grip part, in order to pivot the jaw head. This provides a very ergonomic way of independently controlling the movements of the actuation elements and therefore of the structural elements actuated by the latter, namely the pivoting of the entire jaw head and the pivoting of the one or more jaw parts relative to the jaw head. A rotation of the actuation elements can be effected either by grasping the further control element in the other hand or by using one of the fingers of the hand that is holding the handle.

In another embodiment of the invention, the proximal ends of the actuation elements are connected to drives, of which the control elements effect the movements of the actuation elements.

This measure has the advantage that the movements of the actuation elements can be performed in a controlled manner by motor.

This can easily be achieved, for example, if both the first actuation element and also the second actuation element are provided at their proximal end area with corresponding linear drives that can be actuated via control elements. A further drive, namely a rotary drive, is then provided in order to effect the rotation of the actuation elements. This entire drive can be offered to the operator as a handle on which, for example, the control elements appear as corresponding function buttons via which, for example by symbols, colour markings or corresponding indications, the movements of the actuation elements "forwards and backwards" can be controlled, and a third control element can control the movement "clockwise or anticlockwise rotation".

In another embodiment of the invention, the shaft is mounted rotatably on the handle.

This measure has the advantage of offering yet another degree of freedom, namely rotatability between shaft and handle. The handle, especially if designed like scissors, can be rotated relative to the shaft in order to be better able to adapt the orientation of the latter to local circumstances. The other degrees of freedom remain unaffected by this.

It will be appreciated that the aforementioned features and the features still to be explained below can be used not only in the cited combinations but also in other combinations or singly, without departing from the scope of the present invention.

BRIEF DESCRIPTION OF THE DRAWINGS

The invention is described and explained in more detail below on the basis of a number of selected illustrative embodiments and with reference to the attached drawings, in which:

FIG. 6 shows a side view of the proximal end portion of the second actuation element, which serves to pivot the jaw part, FIG. 7 shows a side view of a second illustrative embodiment of such a second actuation element, FIG. 8 shows a cross section along the line VIII-VIII in FIG. 7, FIG. 9 shows a side view, comparable to the view in FIGS. 6 and 7, of an end portion of a third illustrative embodiment of a second actuation element, wherein an area bounded by a circle in FIG. 9 is shown enlarged and in cross section, FIG. 10 shows a section along the line X-X in FIG. 9.

DETAILED DESCRIPTION OF THE INVENTION

Figure 1:
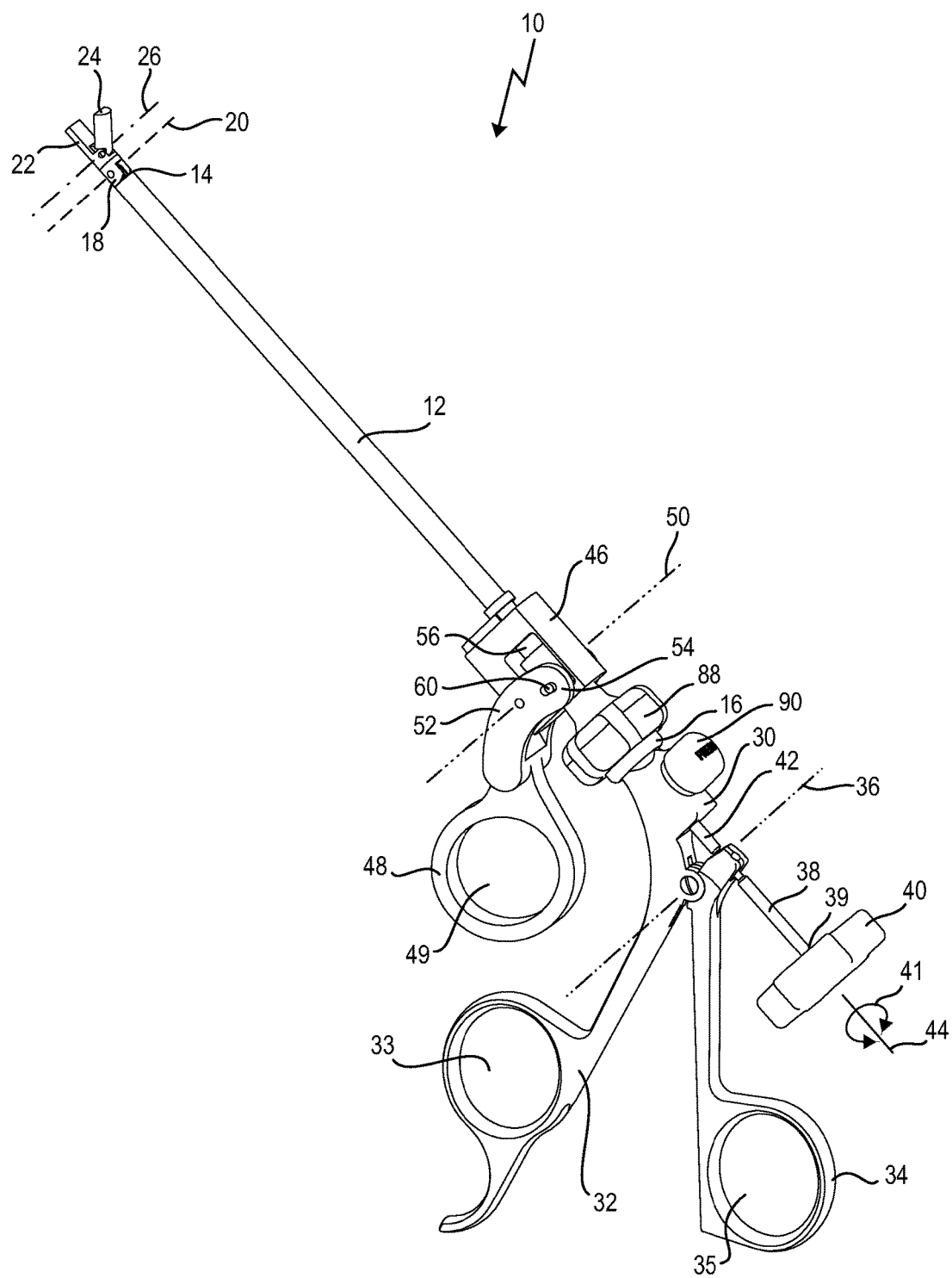
FIG. 1 shows a perspective view of a first illustrative embodiment of a medical instrument, which is designed in the form of forceps with a scissor-like grip part.

A medical instrument shown in FIG. 1 is designated in its entirety by reference number 10.

The instrument 10 has an elongate, stiff hollow shaft 12, which has a distal end 14 and a proximal end 16.

A jaw head 18 is secured on the distal end 14.

The jaw head 18 is arranged on the distal end 14 so as to be pivotable about a first axis 20, which extends transversely with respect to a longitudinal axis 44 of the shaft 12.

The jaw head 18 has a stationary jaw part 22 and a pivotable jaw part 24.

The pivotable jaw part 24 is arranged on the jaw head 18 so as to be pivotable about a second axis 26.

The second axis 26 extends parallel to the first axis 20 and lies distally in front of the first axis 20.

As is explained in more detail below in connection with FIGS. 2 to 5, the entire jaw head 18 is pivotable about the first axis 20, in particular by about 90°, and, in each of these pivot positions, the pivotable jaw part 24 is pivotable about the second axis 26 relative to the jaw head 18, wherein this angle of pivoting is about 45°.

At its proximal end 16, the shaft 12 is connected to a scissor-like handle 30.

The handle 30 has a stationary grip part 32, of which the outer end has a finger eyelet 33. A movable grip part 34, of which the outer end likewise has a finger eyelet 35, is mounted on the stationary grip part 32.

As in a pair of scissors, the two grip parts 32 and 34 are connected via a hinge, wherein the movable grip part 34 can be pivoted about a hinge axis 36.

A second actuation element 38 in the form of a pull/push rod 42 is received in the shaft 12. It extends centrally through the middle of the shaft 12.

The second actuation element 38 extends all the way through the shaft 12 and has a proximal end 39, which protrudes beyond the handle 30. Secured on this proximal end 39 is a rotary knob 40, by which the second actuation element 38, i.e. the pull/push rod 42, can be rotated about the longitudinal axis 44 of the shaft 12, as is indicated in FIG. 1 by an arrow 41.

The movable grip part 34 is designed as a lever, of which the end directed away from the finger eyelet 35 is connected to the pull/push rod 42.

The connection is such that, when the movable grip part 34 is pivoted about the hinge axis 36, the second actuation element 38, or the pull/push rod 42, is moved axially to and fro in the shaft 12. At the same time, the securing is such that this actuation element 38 can be rotated by the rotary knob 40.

For this purpose, for example, the body of the pull/push rod 42 has, in the area where it is connected to the movable grip part 34, a corresponding groove that serves for connection to the movable grip part 34. The flanks of the groove form corresponding abutments for the movable grip part 34, such that the to and fro movement in the axial direction, i.e. along the axis 44, is controlled in this way.

A further movable grip part 48 is arranged in the proximal end area 46 of the shaft 12.

The further grip part 48 likewise has a finger eyelet 49 and is pivotable about a pivot axis 50.

The further grip part 48 is likewise designed as a lever 52, of which the end 54 directed away from the finger eyelet 49 is connected by a pin 60 to a first actuation element 56 in the form of a tubular body 58.

The tubular body 58 is arranged coaxially around the pull/push rod 42, as can be seen in particular from the sectional views in FIGS. 2 to 5.

A laterally protruding pin 60 engages in an oblong hole (not shown in detail here) at the end 54 of the lever 52 and serves to convert the pivoting movement of the further grip part 48 into a linear sliding movement of the first actuation element 56 along the shaft axis 44.

It is clear from the view in FIG. 1 that the grip parts 32, 34 and 48 extend more or less in one plane.

The further grip part 48 lies distally from the stationary grip part 32, whereas the movable grip part 34 extends proximally from the stationary grip part 32.

The movable grip part 48 is a first control element for controlling the axial movement of the first actuation element 56. The movable grip part 38 is a second control element for controlling the axial movement of the second actuation element 38. The rotary knob 40 is a further control element for causing a jointly or common rotation of the two actuation elements 38 and 56.

It is thereby possible, for example, to grasp the handle 30 with one hand such that the middle finger engages in the stationary grip part 32, or in the finger eyelet 33 thereof, and the thumb engages in the finger eyelet 35 of the movable grip part 34.

The index finger or the ring finger of this hand can be placed in the finger eyelet 49 of the further grip part 48.

In this way, using the hand that has grasped the instrument 10, it is possible, by pivoting the movable grip part 34, to move the second actuation element 38 axially to and fro along the shaft axis 44 and, independently of this, to move the first actuation element 56 by pivoting the further grip part 48.

The shaft 12 is designed to be rotatable relative to the handle 30. This rotation can be effected via a rotary wheel 88. A button 90 secures the axial connection between shaft 12 and handle 30 but permits the rotation of the two structural parts relative to each other. By actuating the button 90, the connection between shaft 12 and handle 30 can be closed or opened. The rotation of the jaw head 18 relative to the shaft 12 about the axis 44 is possible in an unlimited manner. The operator can secure the handle 30 in a hold that he finds comfortable, e.g. can close the jaw parts 22, 24 and wind long tissue parts or threads around the jaw area. Without this degree of freedom, the instrument would have to be moved quite far to and fro.

FIGS. 2 to 6 show in more detail the respective design of the actuation elements and of the shaft at the proximal end, or in the jaw head, and show which of the control elements serves to control which structural part.

Figure 3:
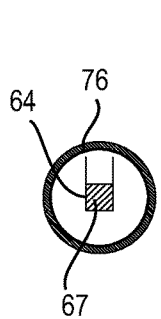
FIG. 3 shows a cross section along the line III-III in FIG. 2.

From the sectional views in FIGS. 2 to 5, it will be seen that the jaw head 18 has a proximal annular body 62 through which there extends a central opening 64 which, as can be seen in particular from the sectional view in FIG. 3, has a square profile. The second actuation element 38, i.e. the pull/push rod 42, has a flexible distal end portion 66 which extends through the opening 64 and which, at least in this area, likewise has a square cross section 67.

A ball head 68 is mounted on the distal end of the flexible distal end portion 66, which ball head 68 is placed in a socket 70 in the body of the pivotable jaw part 24.

Figure 2:
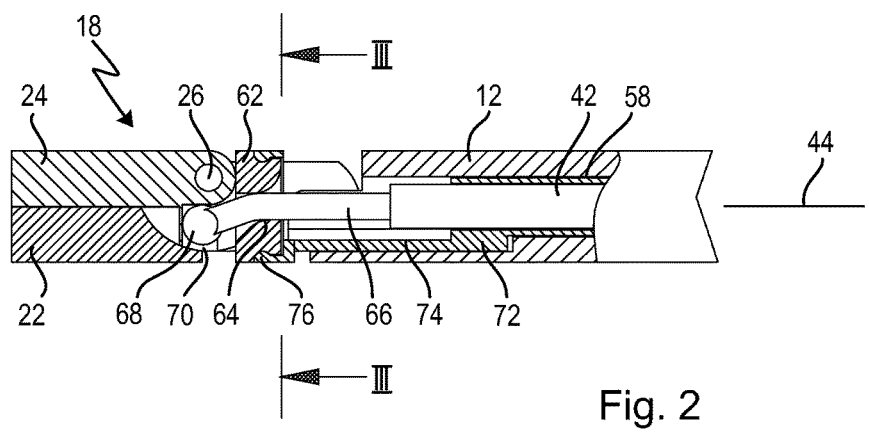
FIG. 2 shows a highly schematic longitudinal section in the distal end area of the instrument from FIG. 1.

As can be seen in particular from the sectional view in FIG. 2, the ball head 68 lies laterally offset from the pivot axis 26 of the pivotable jaw part 24.

For this purpose, it is necessary that the flexible distal end portion 66 curves slightly from the rectilinear central orientation along the shaft axis 44. This curvature starts from, and occurs on the distal side of, the annular body 62, through which this flexible distal end portion 66 extends.

It will also be noted from the sectional view in FIG. 2 that the tubular body 58 of the first actuation element 56 lies tightly around the outside of the second actuation element 38 in the form of the pull/push rod 42.

This tubular body 58 has a distal continuation 72 in the form of an elastic tongue 74, on the outer end of which an annular bead 76 is formed.

This annular bead 76 is fitted from the outside into a circumferential annular groove 78 of the annular body 62.

The securing of the jaw head 18 on the distal end is not shown in the sectional view. It is achieved, as can be seen from FIG. 1, by two fork-like projections which are directed proximally and are pivotable about the first axis 20.

FIG. 2 shows a situation in which the jaw head 18 is located in a linear orientation with respect to the shaft 12 or to the shaft axis 44 of the latter.

Moreover, the jaw parts 22 and 24 are closed, i.e. the pivotable jaw part 24 bears on the stationary jaw part 22, and these likewise extend in the direction of the longitudinal axis 44.

The medical instrument 10 is stowed in this state, for example. The movable grip part 34 of the handle 30 at the same time bears on the stationary grip part 32.

In this state, the distal end of the instrument 10, for example when handled as scissors, can be pushed through an opening in the body.

Figure 4:
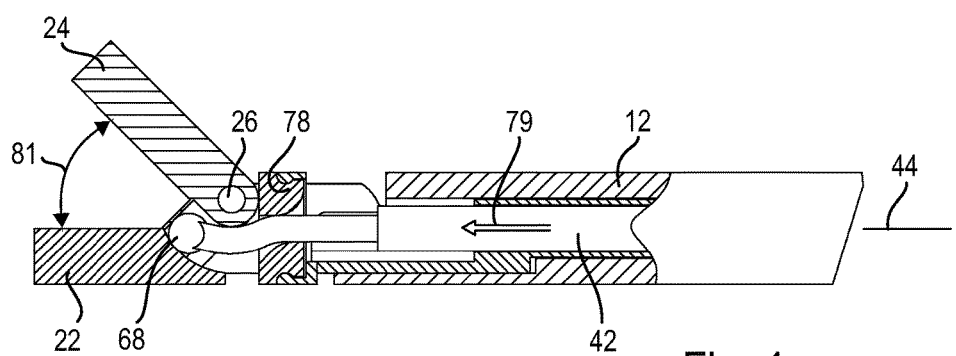
FIG. 4 shows a view corresponding to FIG. 2, but with the movable jaw part opened.

As can be seen from FIG. 4, the pivotable jaw part 24 can be pivoted, i.e. opened, by axial movement of the push/pull rod 42 in the distal direction (see arrow 79). When the pull/push rod 42 is moved in the proximal direction, the pivotable jaw part 24 closes (see double arrow 81).

In the open state shown in FIG. 4, a tissue or a cartilage part that is to be separated can be brought between the opened jaw parts 22 and 24, and it can be separated by closing the jaw parts. The force needed to do this is exerted by the pull/push rod 42. In doing this, the operator moves the movable grip part 34 of the handle 30 towards the stationary grip part 32.

If such a manoeuvre, for example in a nasal cavity or frontal sinus, is to be performed in an area that is not accessible with the rectilinearly outstretched jaw head 18, the latter can be pivoted.

For this purpose, the first actuation element 56, i.e. the tubular body 58, is moved for example in the distal direction (see arrow 85 in FIG. 5), this being controlled by moving the further grip part 48.

Figure 5:
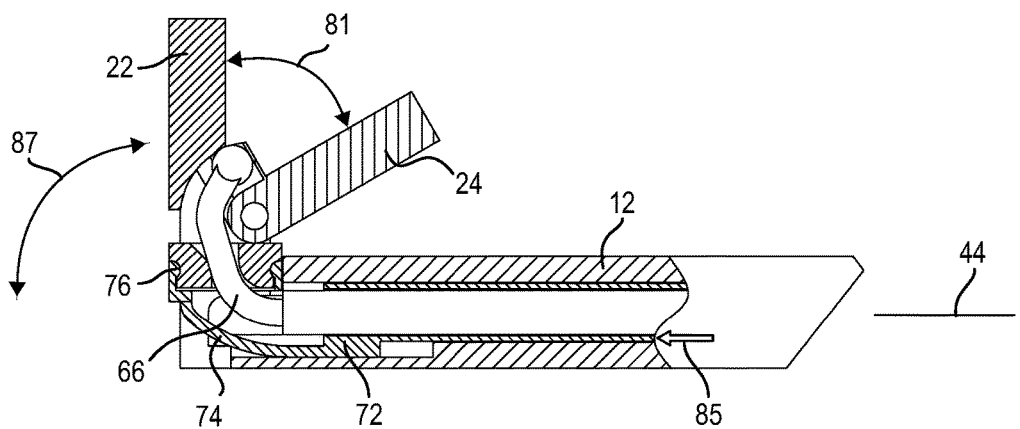
FIG. 5 shows a view corresponding to FIG. 2 and FIG. 4, wherein the jaw head is pivoted out from the shaft axis by 90° from the position shown in FIG. 2 and, in addition, the pivotable jaw part is opened.

Since the tongue 74 extends away from the tubular body 58 about only a certain circumferential area of the latter and is connected to the annular body 62 via the annular bead 76, a movement of the tubular body 58 in the distal direction, as is indicated in FIG. 5 by the arrow 85, has the effect that the entire jaw head 18 is pivoted about the second axis 20, the maximum angle of pivoting being 90° in the illustrative embodiment shown (see double arrow 87).

By virtue of the flexibility of the flexible distal end portion 66 of the pull/push rod 42, this end portion can follow this movement.

From this position, in which the jaw parts 22 and 24 are initially closed, the pivotable jaw part 24 can be pivoted out, i.e. opened, as is shown in FIG. 5. For this purpose, the pull/push rod 42 is simply moved farther in the distal direction, wherein the flexible portion 66 is then pushed through the opening 64 in the annular body 62, and the pivotable jaw part 24 is thus opened. Thus, a tissue section located to one side of the longitudinal extension of the shaft 12 can then be grasped and separated.

It is clear that all of these movements, i.e. the pivoting of the jaw head 18 and the opening and closing of the pivotable jaw part 24, can be carried out independently of each other.

In other words, the pivotable jaw part 24 can be pivoted independently of the position of the jaw head 18, for example from the rectilinear orientation of the jaw head in relation to the shaft axis, as shown in FIG. 2, or from the position of the jaw head 18 pivoted through 90° from the shaft axis, as shown in FIG. 5.

This means that the operator is already afforded quite a few degrees of freedom.

In addition, the assembly composed of jaw head 18 and of the actuation elements 38 and 56 can be rotated about the longitudinal axis 44 of the shaft 12 in each pivot position of the jaw head 18 and in each opening or closing position of the jaw parts 22 and 24.

A further degree of freedom is thus provided, such that the operator can also grasp and separate cartilage sections or tissue sections, for example lying above or below the plane of FIGS. 2 to 5, by means of appropriate rotation about the longitudinal axis.

As has been described at the outset, this is effected quite simply by the rotary knob 40 at the outer end, i.e. proximal end, of the pull/push rod 42.

By virtue of the fact that the cross section 67 of the distal flexible end portion 66 is square, like the opening profile of the opening 64, a rotation movement of the pull/push rod 42 is converted into a rotation movement of the jaw head 18.

To put it another way, these structural elements are thereby connected to each other in a rotationally conjoint manner. This can also be achieved by other polygonal configurations or oval cross-sectional profiles.

As can be seen in particular from FIG. 6, the second actuation element 38, in the central area in which it is received in the shaft 12, can be produced as a rod-shaped body, for example made of plastic or metal or the like. The cross section of the central area of the second actuation element 38 is unimportant as regards the function of the latter. For manufacturing reasons, however, a round cross section is advantageous. Although the central area is preferably in one part, it can, if necessary, also be constructed in several parts.

The flexible distal end portion 66 is likewise designed as a rod-shaped body, but with a square profile, which corresponds to the cross-sectional contour of the opening 64 in the annular body 62.

If the ball head 68 is larger than the opening 64, this can either be made removable or the annular body 62 can be laterally slit, such that the flexible distal end portion 66 can be pushed laterally into the annular body 62.

The annular body 62 itself sits between the two fork-like bodies (see FIG. 1) of the jaw head 18.

The jaw parts 22 and 24 are shown only very schematically in the figures.

They can be designed purely as grasping forceps parts and, for example, can be provided with the appropriate and known ribbings, in order to grasp between them otherwise separated tissue parts.

They can also be designed with axially extending cutting edges, like scissors, in order to cut off or separate tissue parts or cartilage parts.

It is also possible to supply one or both jaw parts 22, 24 with current in order to carry out coagulation processes at the same time.

To ensure that the flexible distal end portion 66 has a sufficient restoring force from the curved position, in order to move as independently as possible to the position shown in FIG. 2, it can be made suitably elastic. Metallic materials or special alloys such as Nitinol, which have a kind of memory, exhibit such properties.

FIGS. 7 and 8 show a second illustrative embodiment of a pull/push rod 92. This essentially consists, at least in the distal end portion 94, of four wires 98 which are placed against one another to form a square and which give the flexible end portion 96 the appropriate flexibility.

The wires 98 could be embedded in the pull/push rod 92 or extend all the way through the latter.

The square formed by the four wires 98 placed against one another can then once again be used to produce the rotationally conjoint connection to the first actuation element and to the jaw head 18 or the annular body 62 of the latter.

FIGS. 9 and 10 show a third illustrative embodiment of a pull/push rod 102. In the area in which it is received in the shaft, the pull/push rod 102 can either be metallic or made of a sufficiently stiff plastic.

The flexible end portion 106 is composed of a square rubber body 108, with a metal wire 110 incorporated in the interior thereof in order to strengthen it and increase the flexibility. In FIG. 9, the enlarged sectional view surrounded by the circle shows how the flexible end portion 106 is embedded.

Here, the wire 110 protrudes beyond the proximal end of the square rubber body 108 and is fitted in a corresponding blind bore in the pull/push rod 102.

The rectangular contour shown in FIG. 10 can then be produced again in order to produce the rotationally conjoint connection to the jaw head 18 or to the other actuation element.

Overall, in an extremely slender design, the high forces required for a separating procedure can easily be provided by the second actuation element 38. The body of the respective pull/push rod 42 can also be made so torsionally stable that the rotary knob 40 for rotating the assembly can be mounted on the proximal end 39 thereof.

The jaw head 18 itself can be made very slender, for example as slender as the outer contour of the shaft 12.

In connection with FIG. 1, a manual operation and control of these movements was described in connection with the instrument 10.

Figure 11:
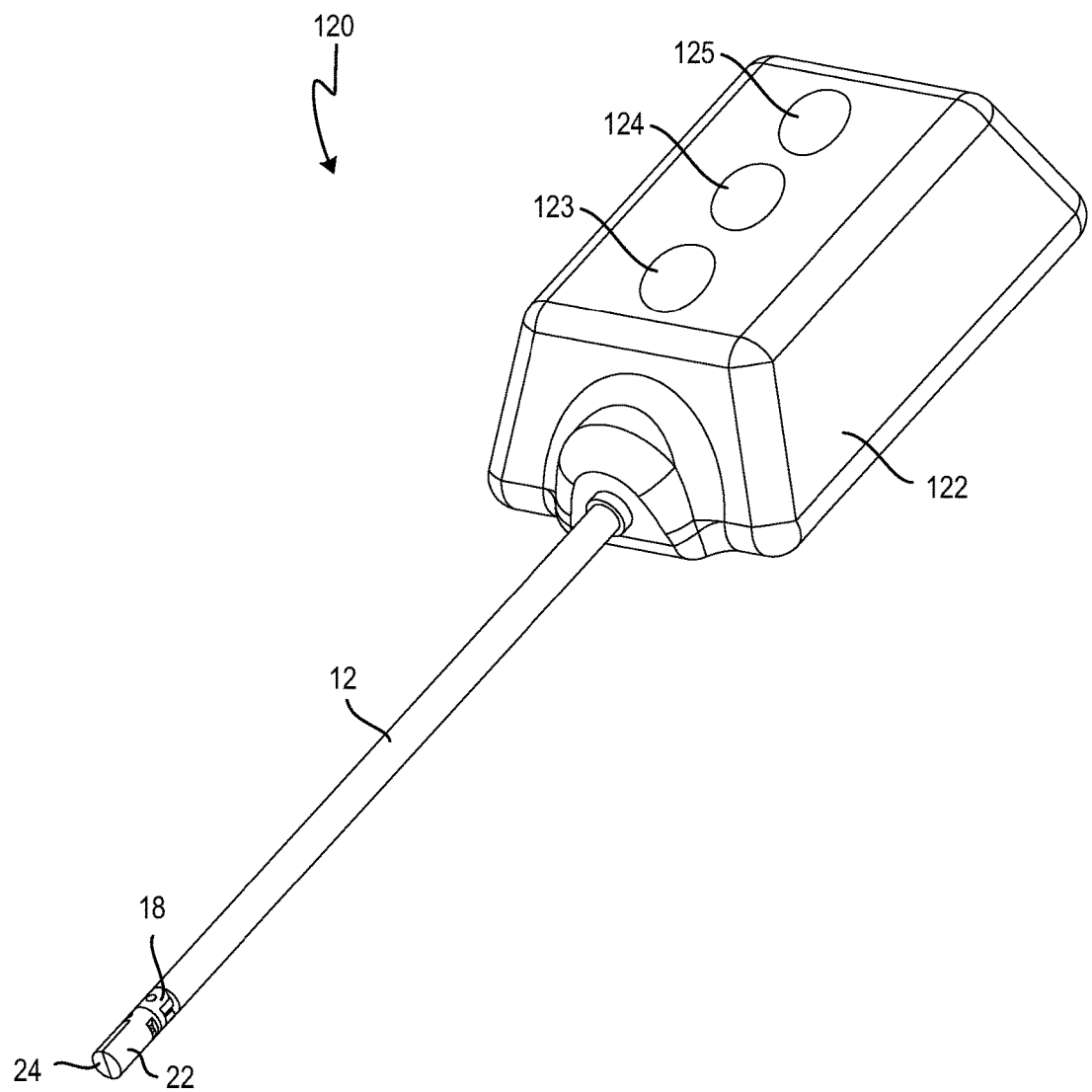
FIG. 11 shows a perspective view of a further illustrative embodiment of an instrument according to the invention, with motorized drive of the actuation elements.

FIG. 11 shows a further illustrative embodiment of such a medical instrument 120, in which motorized drives are arranged at the proximal end.

The shaft 12, the jaw head 18 and the jaw parts 22 and 24 are in principle of the same design as in the illustrative embodiment in FIG. 1.

The proximal ends of the first actuation element and second actuation element are each connected to axial actuating drives which, for example, can be controlled, i.e. actuated, by the control elements 123 and 124.

These control elements 123, 124 can be rotary knobs or toggle switches, by which the movements in the distal direction and proximal direction can be controlled independently of each other, in order either to pivot the jaw head or to open and close the jaw parts 22 and 24.

The control element 125 can then control the rotation movement, i.e. rotation of the assembly clockwise or anticlockwise about the shaft axis 44. For this purpose, a rotary drive is mounted on one of the actuation elements.

This drive 122 is shown only very schematically in FIG. 11. It is also possible to accommodate this drive in a housing shaped like a pistol grip and to provide the control elements 123, 124 and 125 in the corresponding grip depressions or on the outer face.

A medical instrument 10 has a shaft 12, which has a distal end 14 and a proximal end 16, with a jaw head 18 which is arranged at the distal end 14 and is pivotable out from the longitudinal axis 44 of the shaft 12, wherein the jaw head 18 has two jaw parts 22, 24, of which at least one is pivotable, furthermore with a first actuation element 56 for pivoting the jaw head 18, and with at least one second actuation element 38 for pivoting the at least one pivotable jaw part 24, wherein the actuation elements 38, 56 are received in the shaft 12, and with control elements 123, 124, 125 which are arranged at the proximal end 16 of the shaft 12 and are used for controlling the movement of the actuation elements 38, 56. It is proposed that the actuation elements 38, 56 are arranged extending coaxially with respect to each other, and that the actuation elements 38, 56 are received in the shaft 12 so as to be rotatable jointly about the shaft axis 44.

What is claimed is:

1. A medical instrument, comprising:
    a hollow shaft having a distal end and a proximal end;
    a handle directly connected to the proximal end of said shaft;
    a jaw head arranged at said distal end of said shaft,
        said jaw head having two jaw parts, at least one of said two jaw parts is pivotable,
        said jaw head together with said two jaw parts being pivotable out from a longitudinal axis of said shaft,
    a first actuation element for pivoting said jaw head out from said longitudinal axis,
    at least one second actuation element for pivoting said at least one pivotable jaw part,
    said actuation elements are housed in said hollow shaft; and
    a first control element connected to said first actuation element for controlling a movement of said first actuation element;
    wherein said handle includes a second control element connected to said at least one second actuation element for controlling a movement of said at least one second actuation element;
    wherein said jaw head is rotatable relative to said shaft about said shaft axis, while the shaft remains in a present rotation orientation;
    wherein said actuation elements are arranged coaxially with respect to each other within said shaft, and wherein said actuation elements are jointly rotatable about said shaft axis to rotate said jaw head about said shaft axis relative to said shaft; and
    wherein said jointly rotatable actuation elements are arranged to be rotated in and relative to said shaft to rotate said jaw head while the shaft remains in a present rotation orientation.

2. The medical instrument of claim 1, wherein said actuation elements are movable relative to each other, and independently of each other, along said longitudinal axis of said shaft, but are connected to each other for conjoint rotation about said shaft axis.

3. The medical instrument of claim 2, wherein said connection for conjoint rotation is such that a rotation of one of said actuation elements about said axis of said shaft causes a rotation of the other actuation element.

4. The medical instrument of claim 1, wherein an axial movement of said first actuation element can be effected by said first control element, and wherein an axial movement of said at least one second actuation element can be effected independently of a movement of said first actuation element.

5. The medical instrument of claim 4, wherein a further control element is provided, by which further control element a rotation of said actuation elements housed in said shaft can be effected independently of said first control element and said second control element.

6. The medical instrument of claim 4, wherein said second control element comprises a stationary grip part and a movable grip part, wherein said movable grip part being connected to said at least one second actuation element for pivoting said at least one pivotable jaw part and wherein said movable grip part controls a movement of said at least one pivotable jaw part.

7. The medical instrument of claim 6, wherein said stationary grip part and said movable stationary grip part of said second control element are arranged such that they can be grasped by fingers of a hand holding said medical instrument.

8. The medical instrument of claim 6, wherein said shaft being mounted rotatably at said handle to adjust a rotation orientation between said handle and said shaft.

9. The medical instrument of claim 4, wherein said at least one axially displaceable second actuation element for pivoting said at least one pivotable jaw part has a proximal end section, on which proximal end section said second control element is mounted, by which second control element said at least one second actuation element can be rotated about said axis of said shaft.

10. The medical instrument of claim 4, wherein said first control element is mounted on a proximal end area of said shaft, which first control element is designed as a movable grip part, said movable grip part being connected to said first actuation element and controls a movement of said first actuation element.

11. The medical instrument of claim 1, wherein said first actuation element for pivoting said jaw head is arranged coaxially around the one or more actuation elements for pivoting the one or more jaw parts.

12. The medical instrument of claim 1, wherein said actuation elements are coaxially insertable one inside the other along an axial length portion thereof, said axial length portions having a non-circular cross section, which non-circular cross section of said coaxially inserted actuation elements effects a connection for conjoint rotation between said actuation elements.

13. The medical instrument of claim 1, wherein said jaw head has a stationary jaw part and a pivotable jaw part, said pivotable jaw part being connected to a flexible distal end portion of a pull/push rod.

14. The medical instrument of claim 13, wherein said first actuation element for pivoting said jaw head is designed as a tubular body which surrounds said pull/push rod, wherein said tubular body has a flexible distal continuation which is connected to said jaw head to rotate said jaw head about said shaft axis as said actuation elements are jointly rotated about said shaft axis.

15. The medical instrument of claim 1, wherein said first control element is arranged at a proximal end area of said shaft.

16. The medical instrument of claim 1, wherein said at least one of said two jaw parts is pivotable about a first axis, wherein said jaw head together with said two jaw parts is pivotable about a second axis, and wherein said first axis and said second axis are parallel to each other.

17. A medical instrument, comprising:
a hollow shaft having a distal end and a proximal end;
a handle directly connected to the proximal end of said shaft;
a jaw head arranged at said distal end of said shaft,
said jaw head having two jaw parts, at least one of said two jaw parts is pivotable,
said jaw head together with said two jaw parts being pivotable out from a longitudinal axis of said shaft,
a first actuation element for pivoting said jaw head out from said longitudinal axis,
at least one second actuation element for pivoting said at least one pivotable jaw part,
said actuation elements are housed in said hollow shaft; and
a first control element connected to said first actuation element for controlling a movement of said first actuation element;
wherein said handle includes a second control element connected to said at least one second actuation element for controlling a movement of said at least one second actuation element;
wherein said jaw head is rotatable relative to said shaft about said shaft axis, while the shaft remains in a present rotation orientation;
wherein said actuation elements are arranged coaxially with respect to each other within said shaft, and wherein said actuation elements are jointly rotatable about said shaft axis to rotate said jaw head about said shaft axis relative to said shaft;
wherein said jointly rotatable actuation elements are rotatably relative to said shaft; and
wherein said jointly rotatable actuation elements are coaxially insertable one inside the other and provided with a non-circular engagement cross-section in an insertion section therebetween.

18. A medical instrument, comprising:
a hollow shaft having a distal end and a proximal end;
a handle directly connected to the proximal end of said shaft;
a jaw head arranged at said distal end of said shaft,
said jaw head having two jaw parts,
said jaw head together with said two jaw parts being pivotable out from a longitudinal axis of said shaft,
a first actuation element for pivoting said jaw head out from said longitudinal axis,
at least one second actuation element for pivoting said at least one pivotable jaw part,
said actuation elements are housed in said hollow shaft; and
a first control element connected to said first actuation element for controlling a movement of said first actuation element;
wherein said handle includes a second control element connected to said at least one second actuation element for controlling a movement of said at least one second actuation element;
wherein said jaw head is rotatable relative to said shaft about said shaft axis, while the shaft remains in a present rotation orientation;
wherein said actuation elements are arranged coaxially with respect to each other within said shaft, and wherein said actuation elements are jointly rotatable about said shaft axis to rotate said jaw head about said shaft axis relative to said shaft;
wherein said jointly rotatable actuation elements are rotatably relative to said shaft;
wherein one of said two jaw parts is attached to said jaw head to be pivoted with said jaw head as said jaw head is pivoted; and
wherein the other one of said two jaw parts is pivotable with respect to the other jaw part, independently of the position of the jaw head.

* * * * *